(12) United States Patent
Kaufman et al.

(10) Patent No.: US 6,659,963 B2
(45) Date of Patent: Dec. 9, 2003

(54) APPARATUS FOR OBTAINING TEMPERATURE AND HUMIDITY MEASUREMENTS

(75) Inventors: Jonathan W. Kaufman, Leonardtown, MD (US); Gregory K. Askew, St. Inigoes, MD (US); Kambiz Farahmand, Corpus Christi, TX (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 16 days.

(21) Appl. No.: 10/056,811

(22) Filed: Jan. 24, 2002

(65) Prior Publication Data

US 2003/0139685 A1 Jul. 24, 2003

(51) Int. Cl.$^7$ .................................................. A61B 5/00
(52) U.S. Cl. ........................ 600/549; 600/537; 73/25.01
(58) Field of Search ............................... 600/474, 549, 600/593, 587, 529, 537; 374/148, 166, 179; 73/25.01, 25.04

(56) References Cited

U.S. PATENT DOCUMENTS 5,069,222 A * 12/1991 McDonald, Jr. ............ 600/537
5,365,940 A * 11/1994 Teves .......................... 600/549
2001/0053882 A1 * 12/2001 Haddock et al. ............ 600/549
2002/0048310 A1 * 4/2002 Heuser ........................ 374/141
2003/0013987 A1 * 1/2003 Saadat ........................ 600/549

* cited by examiner

Primary Examiner—Eric F. Winakur
Assistant Examiner—Jonathan Foreman
(74) Attorney, Agent, or Firm—Ron Billi

(57) ABSTRACT

A probe for obtaining temperature and humidity readings within the oral and nasal cavity. An elongated tube having a wire cage at one of its ends, includes first and second longitudinally positioned pairs of thermocouples, one thermocouple of each pair having a wetted wick for obtaining humidity measurements. The pairs of thermocouples are positioned within the confines of the wire cage such that temperature and humidity measurements are made of the subject's airway. Other longitudinally positioned thermocouples are outside the confines of the wire cage and are used to obtain surface temperature readings. For positioning inside the relatively small nasal cavity, one embodiment is constructed and arranged to reduce the outside dimension of the cage for ease of insertion and to return it to its original dimension after insertion, so that the thermocouples outside the confines of the wire cage can contact the nasal membrane.

22 Claims, 6 Drawing Sheets

APPARATUS FOR OBTAINING TEMPERATURE AND HUMIDITY MEASUREMENTS

STATEMENT OF GOVERNMENT INTEREST

The invention described herein may be manufactured and used by or for the Government of the United States of America for government purposes without the payment of any royalties therefor.

BACKGROUND OF THE INVENTION

In fields such as physiology, medical, and respiratory studies, it is often required to collect thermal data within the airways of a subject, such as a human, or other breathing animal. Such data can be used to obtain heat and mass transfer properties of the airway and tan be used in the evaluation of intra-airway vascular responses to environmental and pharmaceutical stimuli, by way of example.

The present invention provides a thermal probe which can rapidly acquire thermal and humidity data relative to inspired and expired breathing gas, including air, in the airway of a subject for evaluation purposes in such studies. Although the invention will be described with respect to a human subject, the apparatus is equally applicable for obtaining temperature and humidity readings within a conduit.

SUMMARY OF THE INVENTION

A temperature probe is provided for obtaining thermal measurements within a conduit such as the airway of a subject. The probe includes an elongated tube extending along a longitudinal axis and having a wire cage at the end which is inserted into the airway. At least first and second sensor arrangements are longitudinally disposed on the outside of the tube, within the confines of the cage, for obtaining an indication of airway humidity and temperature. In one embodiment each sensor arrangement includes a dry-bulb thermocouple and a wet-bulb thermocouple. A plurality of longitudinally disposed temperature sensors extend outside of the confines of the cage and are adapted to contact the inner surface of the airway for obtaining surface temperatures. All of the sensor outputs are coupled to an interface connector array whereby the output signals may be provided to an analyzing system. For measurements in the nasal airway, the cage portion may be reduced in size for insertion and thereafter expanded so that the sensors make contact with the mucous membrane of the nose.

BRIEF DESCRIPTION OF THE DRAWINGS

The invention will be better understood, and further objects, features and advantages thereof will become more apparent from the following description of the preferred embodiment, taken in conjunction with the accompanying drawings, in which.

DETAILED DESCRIPTION OF THE PREFERRED EMBODIMENTS

Figure 1:
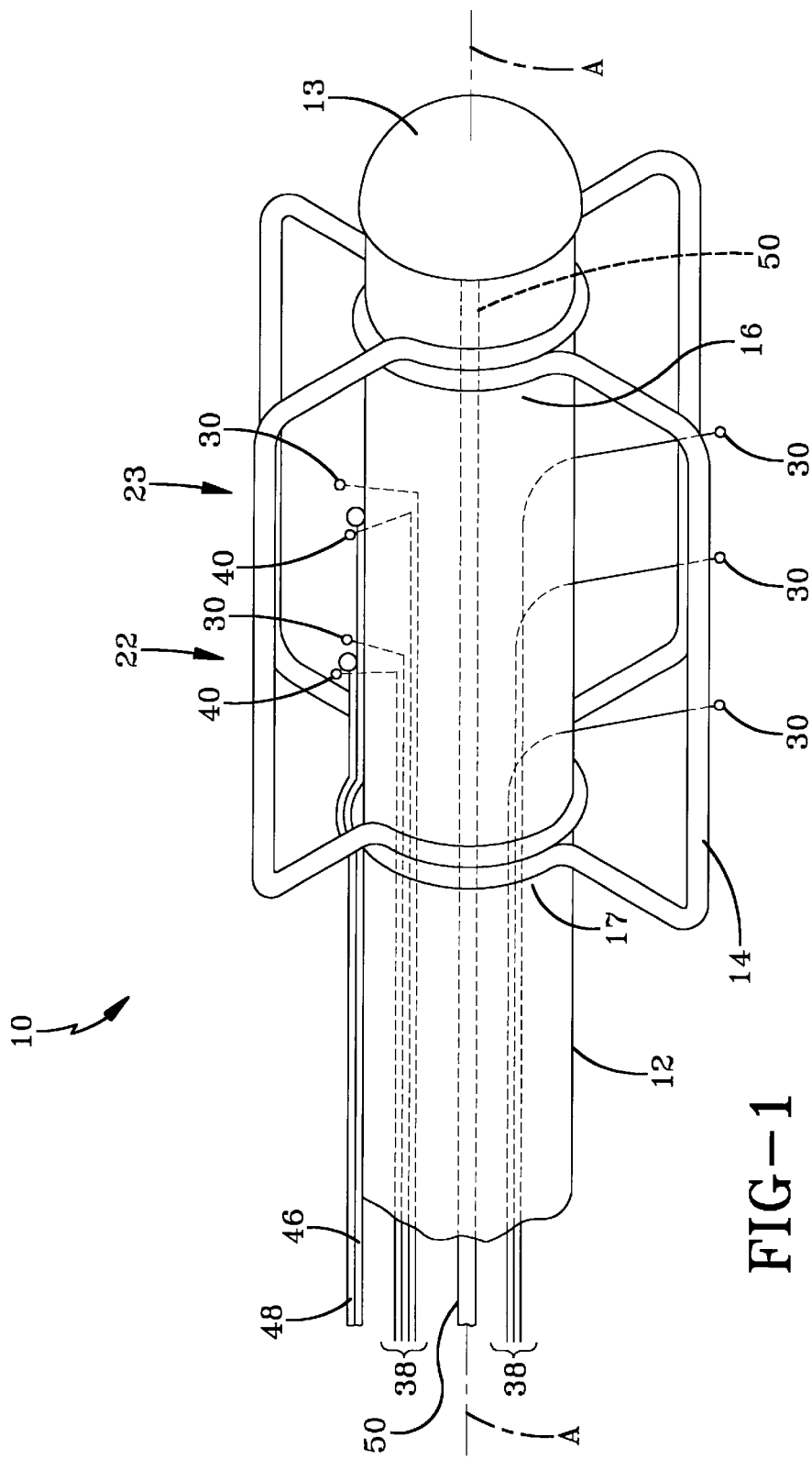
FIG. 1 illustrates a probe in accordance with one embodiment of the invention, for insertion into the oral cavity of a subject.

In the drawings, which are not necessarily to scale, like or corresponding parts are denoted by like or corresponding reference numerals.

The oral cavity temperature probe 10 of FIG. 1 includes a elongated tube 12 which extends along a longitudinal axis A—A and is closed at its tip by means of a seal 13 to isolate the wire-carrying inside of the tube, for cleaning and sterilization purposes. A wire cage 14, located near the tip of probe 10, is provided to prevent the bending and pushing out of position various temperature sensors, when the probe is being handled, or during actual measurements. The distal end 16 of cage 14 is wrapped around, and connected to tube 12, as is the proximal end 17 of the cage. The wires of the cage, by way of example, may be of a metal or plastic material which is relatively stiff for the embodiment of FIG. 1, or, as will be seen, relatively flexible, for the embodiment of FIG. 7.

The probe 10 includes at least two longitudinally displaced sensor arrangements 22 and 23 on the outside of the tube and within the confines of the cage 14 for obtaining indications of airway temperature and humidity. Although a humidity sensor may be used in the sensor arrangement, wet-bulb and dry-bulb thermal sensors such as thermocouples, will be used, by way of example, and to this end additional reference is made to FIGS. 2 and 3.

Figure 2:
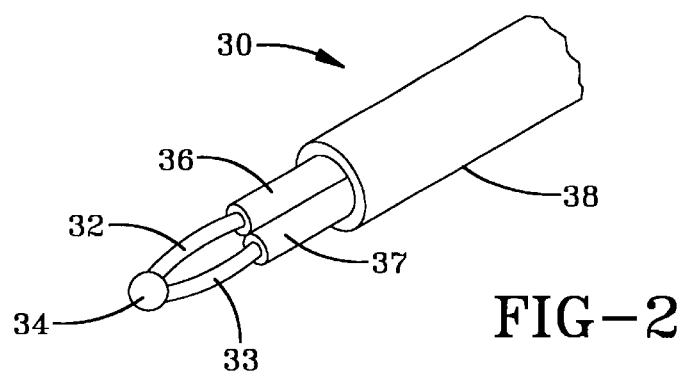
FIG. 2 illustrates one type of temperature sensor which may be utilized in the present invention.

FIG. 2 illustrates a typical dry-bulb thermocouple 30 which is comprised of two dissimilar metal wires 32 and 33, such as copper and constantan, respectively. These wires are welded together at their ends to form a bead 34, the arrangement providing a small voltage indicative of the temperature to which the bead is subjected. The wire 32 is provided with insulation 36, the wire 33 is provided with insulation 37, and the two are encased in a protective jacket 38.

Figure 3:
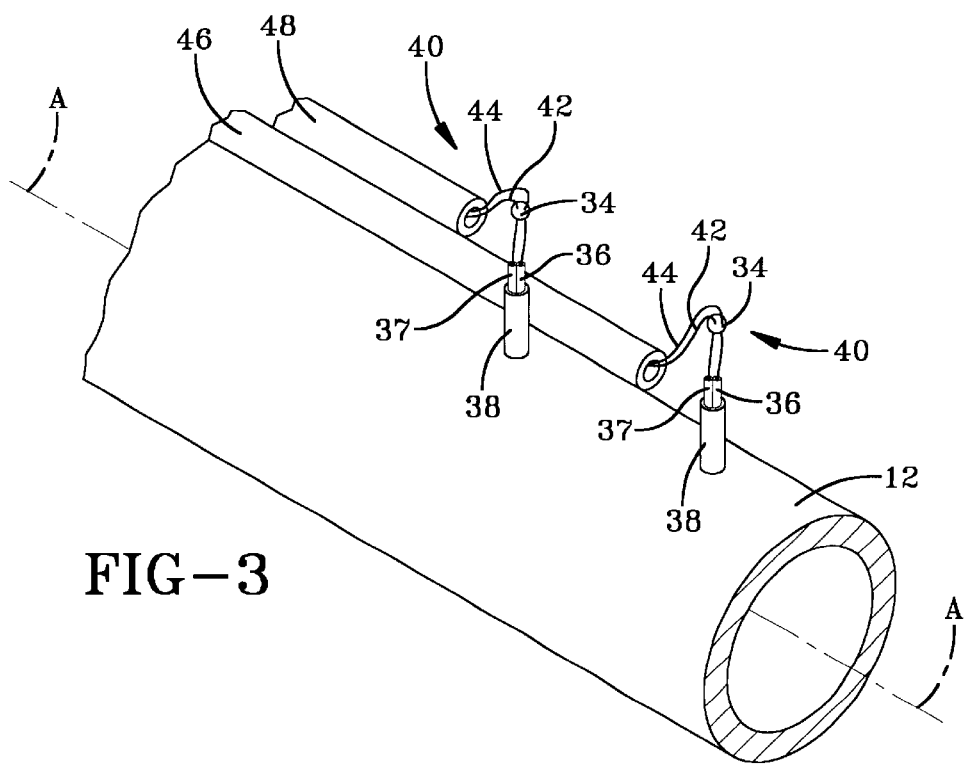
FIG. 3 illustrates one type of humidity sensor which may be utilized in the present invention.

FIG. 3 illustrates a portion of the front of tube 12 (without the wire cage 14). A typical wet-bulb thermocouple 40, two of which are illustrated in FIG. 3, is comprised of a dry-bulb thermocouple, as in FIG. 2, with the addition of a wick 42, such as of cotton, covering the bead 34 and connected to a supply of distilled water by means of cotton strands 44. Cotton strands 44 from the forward wet-bulb thermocouple 40 are supplied with water from a capillary tube 46, and cotton strands 44 from the rearward wet-bulb thermocouple 40 are supplied with water from a capillary tube 48.

By way of example, for a small thermocouple having a bead diameter of around 0.06 mm, such as model W-TW-44P, of Physitemp Instruments, Inc. of Clifton N.J., the wick 42 covering the bead 34 may consist of 3 strands of 100% cotton string from medical gauze tied around bead 34 and trimmed to reduce mass and assure minimum response time. The cotton strands are also used to carry the water from the capillary tubes 46 and 48, the ends of which are positioned no more than around 1 cm from a respective wet-bulb thermocouple. The arrangement assures that a water droplet is not formed around the thermocouple bead and yet the wick remains saturated with water.

Returning once again to FIG. 1, the probe additionally includes two dry-bulb thermocouples 30 proximate the wet-bulb thermocouples 40, to be used in obtaining relative humidity readings in the airway of a subject as well as airway temperature. A plurality, three in the example, of longitudinally arranged dry-bulb thermocouples 30 are also included (seen on the underside of tube 12) and these thermocouples are arranged to extend outside of the confines of wire cage 14 so as to be able to contact and measure surface temperatures within the oral cavity.

If tube 12 is relatively flexible, such as Teflon tubing, an internal support wire 50 is provided and extends along the longitudinal axis A—A to connect with seal 13. Such support wire 50 may be used as a handle for probe manipulation, and allows the tubing to be bent to the shape of the subject's cheek inside the oral cavity to maintain proper positioning of the surface temperature thermocouple. If tube 12 is of a material which is relatively stiff, yet bendable, the support wire 50 may not be needed.

Figure 4:
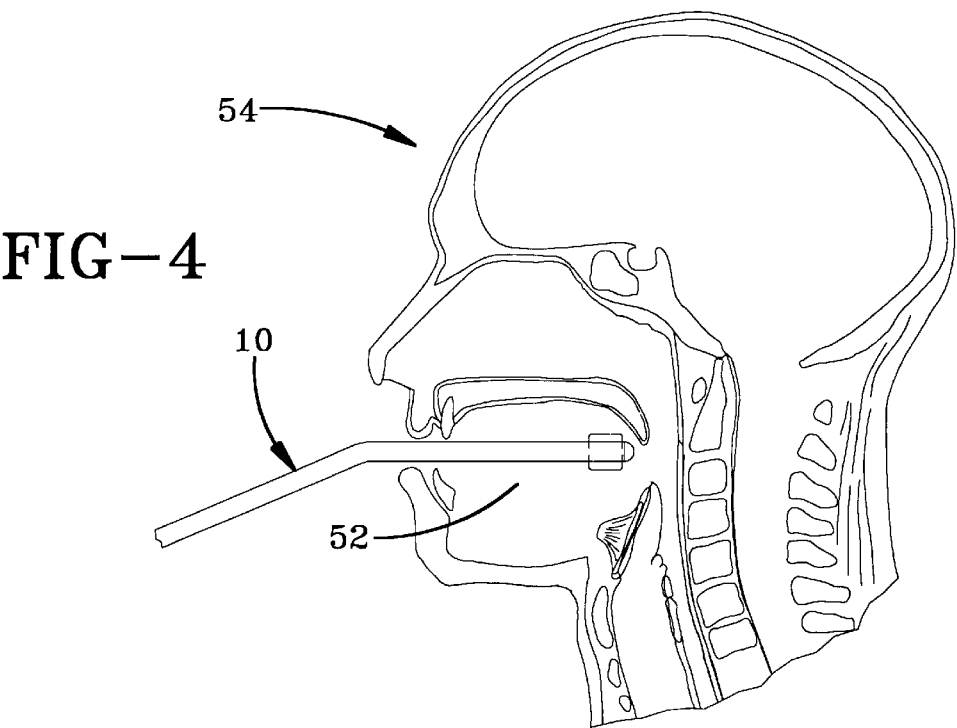
FIG. 4 illustrates the probe of FIG. 1 inserted into the oral cavity of a person.
Figure 5:
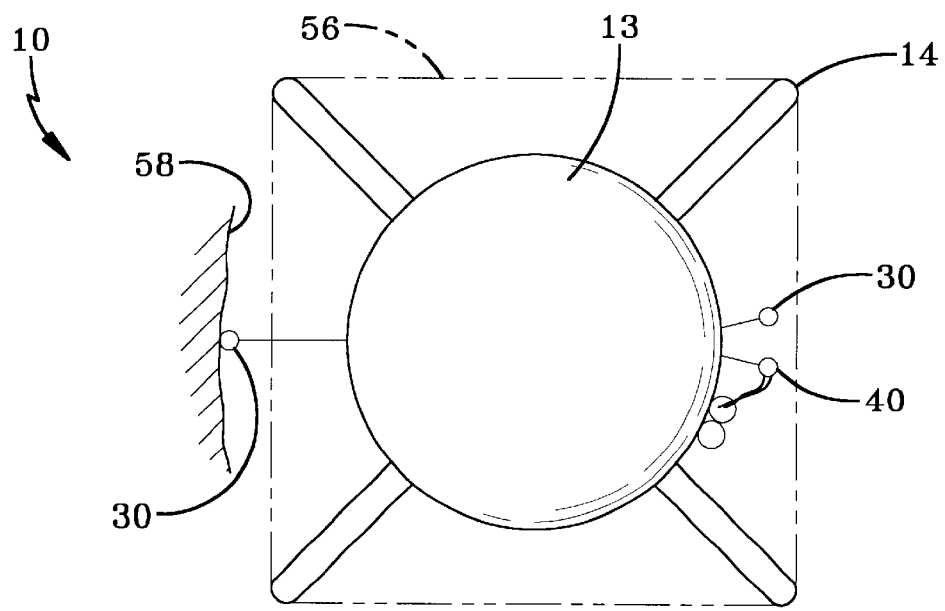
FIG. 5 is an end view of the probe of FIG. 1.

FIG. 4 illustrates the insertion of probe 10 into the oral cavity 52 of a subject 54 and FIG. 5 illustrates an end view of the probe 10. Dot-dash line 56 defines the confines of wire cage 14 and it is seen that wet-bulb thermocouples 40 paired with dry-bulb thermocouples 30 are within the confines defined by dot-dash line 56 and thus do not touch any oral cavity surfaces, and are used for airway measurements, while dry-bulb thermocouples 30 extending outside of the confines are in contact with an oral cavity buccal surface 58.

Figure 6:
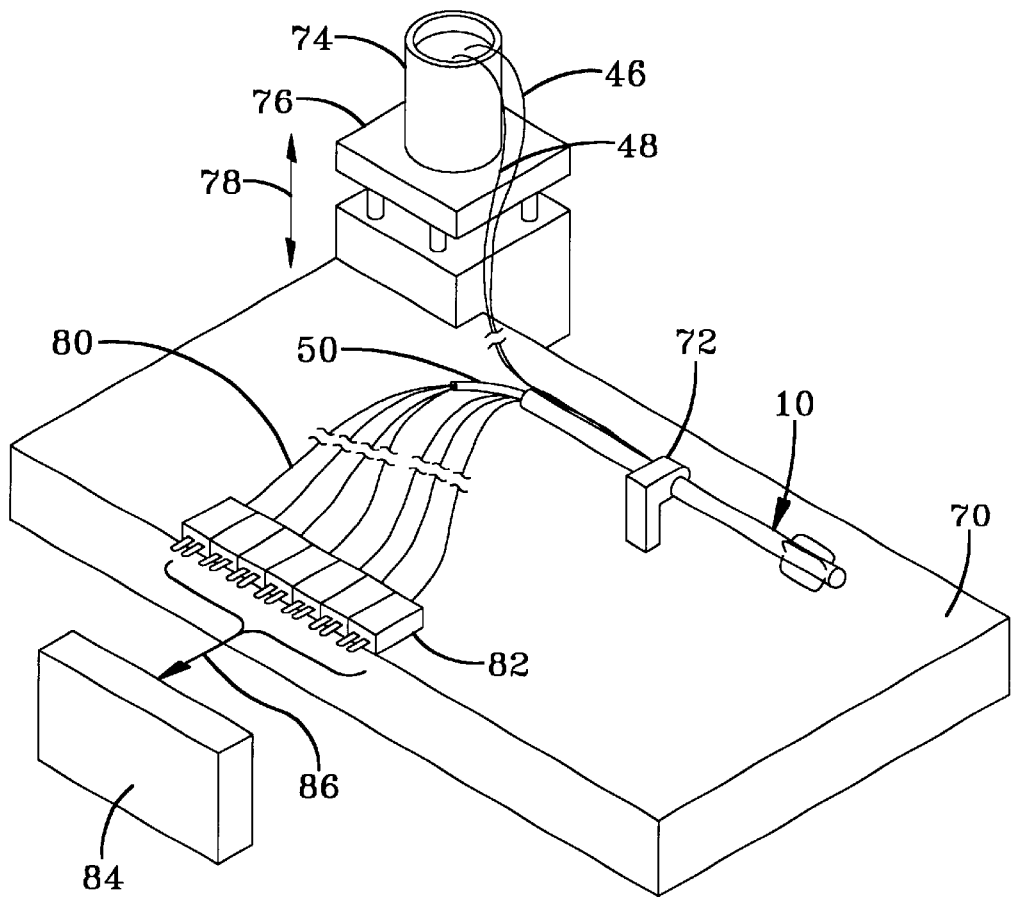
FIG. 6 is a view of apparatus for supporting the function of the probe of FIG. 1.

Support equipment which allows for the probe apparatus to be carried to a measurement location is illustrated in FIG. 6. The support equipment includes a base 70, having an upstanding clip 72 for holding the probe 10. A water reservoir 74 holds a supply of distilled water for delivery to the wet-bulb thermocouples, via capillary tubes 46 and 48, and is situated on a stand 76. To adjust the hydrostatic pressure for water delivery, the stand 76 may be made moveable in a vertical direction, as indicated by arrow 78. Leads, designated by numeral 80, from all of the seven thermocouples used in the embodiment of FIG. 1 are provided to an interface connector block 82 whereby the thermocouple signals are delivered to an analyzing system 84, via a harness assembly 86.

Figure 7:
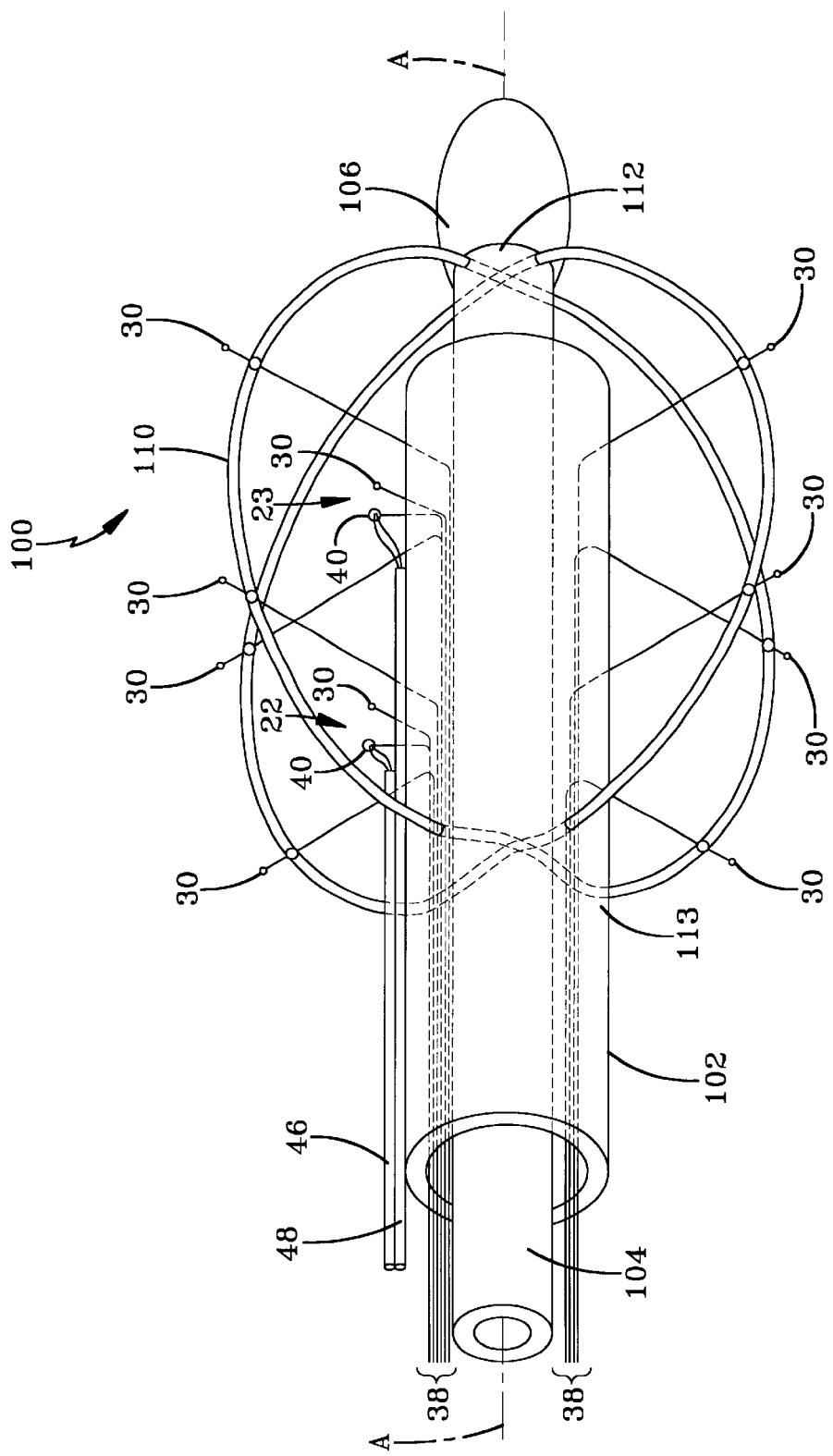
FIG. 7 illustrates an embodiment of the invention for insertion into the nasal cavity of a subject.

FIG. 7 illustrates an embodiment of the present invention utilized for obtaining thermal measurements in the nasal cavity of a subject. The probe 100 includes an elongated outer tube 102 and a coaxial inner tube 104 closed at its distal end by a seal 106. A wire cage 110 has its distal end 112 connected to inner tube 104, whereas the proximal end 113 of the wire cage 110 is connected to the outer tube 102.

In a manner similar to probe 10 of FIG. 1, the probe 100 includes at least first and second sensor arrangements longitudinally disposed, for obtaining humidity and temperature readings in the nasal airway. The sensor arrangements are, by way of example, the same wet-bulb thermocouple and dry-bulb thermocouple system of FIG. 1. In addition, probe 100 includes a plurality of dry-bulb thermocouples 30 for obtaining surface temperatures. Eight dry-bulb thermocouples 30 are arranged outside of the cage confines in a manner that a pair of forward and rearward thermocouples are carried by each wire of the wire cage 110.

Inner tube 104 projects past the end of outer tube 102 and is axially moveable with respect to the outer tube 102. When the inner tube 104 is moved forward relative to outer tube 102, the wire cage 110 elongates due to the distal and proximal ends 112 and 113 being connected to the different tubes. This elongation reduces the outside dimension of the wire cage 110, allowing it to be inserted into the relatively small nasal cavity of a subject. After insertion the inner tube 104 may be moved backwards to the position shown in FIG. 7. The wire cage 110 then assumes its normal dimension whereby the thermocouples 30 connected to the wires of cage 110 and outside the confines of the cage, will contact the mucous membrane of the nasal cavity.

Figure 8:
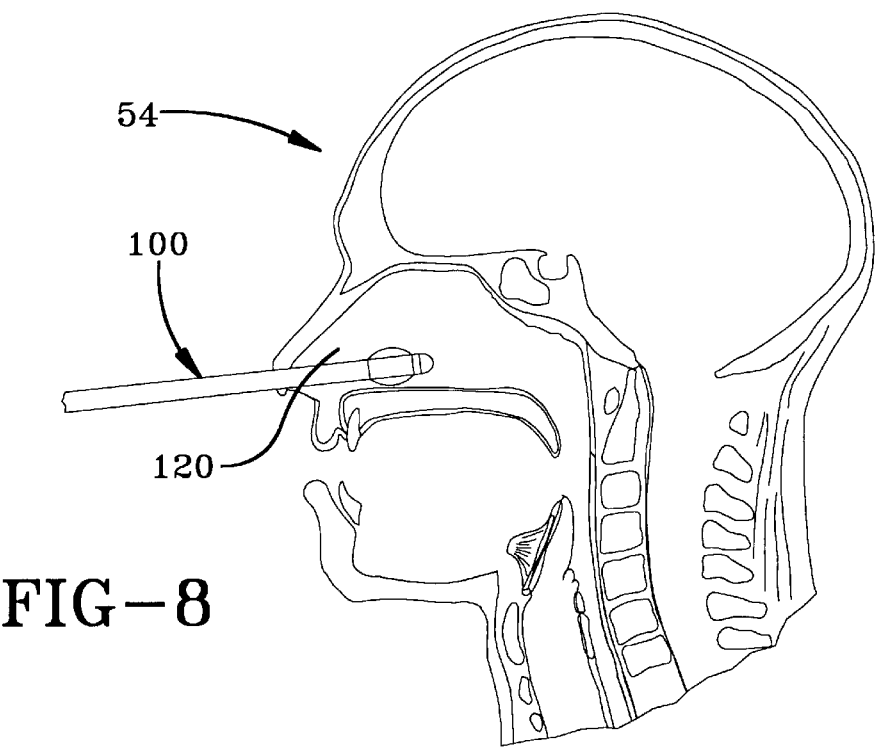
FIG. 8 illustrates the probe of FIG. 7 inserted into the nasal cavity of a person.
Figure 9:
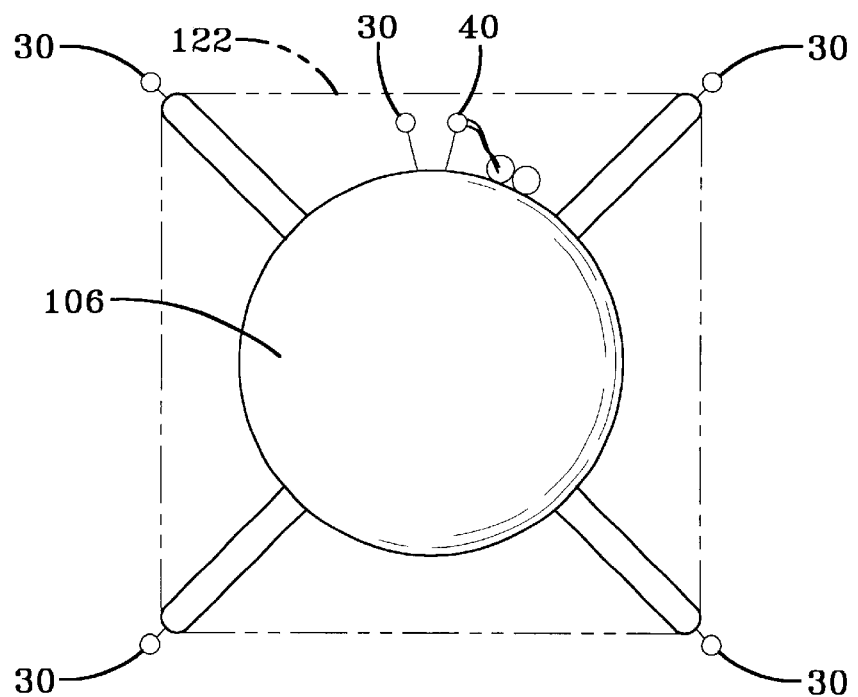
FIG. 9 is an end view of the probe of FIG. 7.

FIG. 8 illustrates the insertion of probe 100 into the nasal cavity 120 of the subject 54 and FIG. 9 illustrates an end view of the probe 100. One pair of wet-bulb thermocouple 40 and dry-bulb thermocouple 30 is seen within the confines of the wire cage 110, as defined by the dot-dash line 122. The remainder of the dry-bulb thermocouples 30 are attached to the outside of the wires of the cage 110, by which the thermocouples will contact the inside surfaces of the nose and provide multiple readings at equal intervals along the nasal cavity at 0, 90, 180 and 270 degree locations. The support equipment for the probe 100 is identical to that illustrated in FIG. 6 for probe 10, with the addition of five interface connectors in the connector block 82, to accommodate all of the 12 thermocouples used.

It will be readily seen by one of ordinary skill in the art that the present invention fulfills all of the objects set forth herein. After reading the foregoing specification, one of ordinary skill in the art will be able to effect various changes, substitutions of equivalents and various other aspects of the present invention as broadly disclosed herein. It is therefore intended that the protection granted hereon be limited only by the definition contained in the appended claims and equivalents. Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included.

What is claimed is:

1. Apparatus for obtaining temperature and humidity measurements within a conduit, having an inner surface, comprising:
   an elongated tube extending along a longitudinal axis and having a wire cage at one end thereof;
   at least first and second sensor arrangements longitudinally disposed on the outside of said tube and within the confines of said cage, for obtaining an indication of conduit temperature and humidity;
   a plurality of longitudinally disposed temperature sensors extending outside the confines of said cage and adapted to contact the inner surface of said conduit for obtaining surface temperature measurements; and
   interface connectors connected to said temperature sensors and sensors disposed within said sensor arrangements for providing output signals to an analyzing system.

2. Apparatus according to claim 1 wherein:
said conduit is an airway of a breathing subject.

3. Apparatus according to claim 2 wherein:
said breathing subject is a human.

4. Apparatus according to claim 1 wherein:
said temperature sensors are thermocouples.

5. Apparatus according to claim 1 wherein:
said elongated tube is relatively flexible; and which includes a support wire extending along said longitudinal axis within said elongated tube to allow said elongated tube to assume a bent position and to maintain said bent position.

6. Apparatus according to claim 1 which includes:

a seal at the one end of said elongated tube.

7. Apparatus according to claim 1 which includes:

a second tube coaxially positioned, and longitudinally moveable, within said elongated tube, and extending past the one end thereof;

said wire cage having a distal end and a proximal end;

said distal end being connected to said second tube;

said proximal end being connected to said elongated tube, whereby forward movement of said second tube will cause said wire cage to reduce its outer dimension.

8. Apparatus according to claim 1 wherein:

each of said plurality of longitudinally disposed temperature sensors is positioned on the outside of a wire of said wire cage.

9. Apparatus according to claim 8 wherein:

a pair of said temperature sensors, one forward and one rearward, is positioned on each said wire.

10. Apparatus according to claim 7 which includes:

a seal at the end of said second tube.

11. Apparatus for obtaining temperature and humidity measurements within a conduit, having an inner surface, comprising:

an elongated tube extending along a longitudinal axis and having a wire cage at one end thereof;

at least first and second sensor arrangements longitudinally disposed on the outside of said tube and within the confines of said cage, for obtaining an indication of conduit temperature and humidity, each of said first and second sensor arrangements including a pair of temperature sensors, one temperature sensor of said pair being covered by a wick and including a wetting arrangement for wetting said wick;

a plurality of longitudinally disposed temperature sensors extending outside the confines of said cage and adapted to contact the inner surface of said conduit for obtaining surface temperature measurements; and interface connectors connected to said temperature sensors and sensors disposed within said sensor arrangements for providing output signals to an analyzing system.

12. Apparatus according to claim 11 wherein:

said wetting arrangement includes a source of liquid, a capillary tube connected at one end thereof to said source of liquid and said wick being in liquid communication with the other end of said capillary tube.

13. Apparatus according to claim 12 wherein:

said liquid is distilled water.

14. Apparatus according to claim 11 wherein:

said conduit is an airway of a breathing subject.

15. Apparatus according to claim 14 wherein:

said breathing subject is a human.

16. Apparatus according to claim 11 wherein:

said temperature sensors are thermocouples.

17. Apparatus according to claim 11 wherein:

said elongated tube is relatively flexible; and which includes a support wire extending along said longitudinal axis within said elongated tube to allow said elongated tube to assume a bent position and to maintain said bent position.

18. Apparatus according to claim 11 which includes:

a seal at the one end of said elongated tube.

19. Apparatus according to claim 11 which includes:

a second tube coaxially positioned, and longitudinally moveable, within said elongated tube, and extending past the one end thereof;

said wire cage having a distal end and a proximal end;

said distal end being connected to said second tube;

said proximal end being connected to said elongated tube, whereby forward movement of said second tube will cause said wire cage to reduce its outer dimension.

20. Apparatus according to claim 19 wherein:

each of said plurality of longitudinally disposed temperature sensors is positioned on the outside of a wire of said wire cage.

21. Apparatus according to claim 20 wherein:

a pair of said temperature sensors, one forward and one rearward, is positioned on each said wire.

22. Apparatus according to claim 19 which includes:

a seal at the end of said second tube.

* * * * *